United States Patent [19]

George et al.

[11] Patent Number: 5,977,250

[45] Date of Patent: Nov. 2, 1999

[54] LATEX OF POLYHYDROXYALKANOATE

[75] Inventors: Neil George, Leeds; Timothy Hammond; John MacDonald Liddell, both of Stockton on Tees; Rajasingham Satgurunathan, Kingsley, all of United Kingdom; Peter Deryk Turner, County Waterford, Ireland

[73] Assignee: Monsanto Company, St. Louis, Mo.

[21] Appl. No.: 08/875,976

[22] PCT Filed: Feb. 9, 1996

[86] PCT No.: PCT/GB96/00284

§ 371 Date: Nov. 24, 1997

§ 102(e) Date: Nov. 24, 1997

[87] PCT Pub. No.: WO96/24682

PCT Pub. Date: Aug. 15, 1996

[30] Foreign Application Priority Data

Feb. 9, 1995 [GB] United Kingdom .................... 9502521
Feb. 9, 1995 [GB] United Kingdom .................... 9502522
Feb. 9, 1995 [GB] United Kingdom .................... 9502531
May 16, 1995 [GB] United Kingdom .................... 9509857

[51] Int. Cl.⁶ ................... C08L 67/04; C08G 63/06; C08H 5/00; C12P 7/62
[52] U.S. Cl. ................... 524/845; 528/361; 527/202; 427/391
[58] Field of Search ................... 524/845; 528/361; 527/202; 427/391

[56] References Cited

U.S. PATENT DOCUMENTS 5,451,456  9/1995  Marchessault et al. ................ 428/327

FOREIGN PATENT DOCUMENTS

WO 94/07940  4/1994  WIPO ................................ C08J 3/12
WO 95/15260  6/1995  WIPO ............................ B32B 23/08

OTHER PUBLICATIONS

STN Iternational, Derwent Information, Ltd., WPIDS accession No. 95–157857, Denki Kagaku Kogyo KK: "Isolation and purificn. of poly hydroxy–alkanoate used as coating agent—from microorganisms, using surfactant to control poly hydroxy–alkanoate in amorphous condition."
Koning, G.J.M., et al., "Biosynthesis of Poly–(R)–3–hyudroxyalkanoate: An Emulsion Polymerization," 1:223–226, 1993.

Primary Examiner—Tae Yoon
Attorney, Agent, or Firm—Gary M. Bond; Arnold, White & Durkee

[57] ABSTRACT

A chiral (R) stereospecific polyhydroxyalkanoate (PHA) in aqueous latex form having virgin disperse phase particles of very low or undetectable crystallinity is useful in making a water-sensitive structure water-resistant. It may be used as a mixture with a latex of a synthetic polymer. Processes for making the PHA latex are disclosed.

6 Claims, No Drawings

LATEX OF POLYHYDROXYALKANOATE

This invention relates to particulate polyester, to polyhydroxyalkanoate (PHA) in preferred forms and processes for making it, and to a structure having PHA as coating or binder.

PHA, the general formula of which is set out below, is accumulated by many micro-organisms, particularly bacteria, for example of the genera Alcaligenes, Athiorhodium, Azotobacter, Bacillus, Nocardia, Pseudomonas, Rhizobium, and Spirillium, as an energy reserve material. It is conveniently prepared by cultivating the micro-organism in an aqueous medium on an energy and carbon source. At least part of the cultivation is preferably conducted under limitation of a nutrient essential for growth but not required for PHA accumulation. Examples of suitable processes are described in EP-A-15669 and 46344.

Such PHAs containing both 3-hydroxybutyrate (HB) units alone or with 3-hydroxyvalerate (HV) units are available commercially. Such PHAs containing larger repeating units have been described.

In the paper by Marchessault et al. (Report of NATO Advanced Research Workshop at Sitges, Spain 26–31 May 1990, 'Novel biodegradable microbial polymers; ed. Dawes, publ. Kluwer) there is disclosed a latex of a PHA, namely polyhydroxybutyrate-co-valerate (PHBV 21% V) supplied by a predecessor of the present applicant in which x-ray diffraction shows some crystalline diffraction in the PHB lattice. Further relevant work by this author along with various co-authors is described in other publications, including Polymer 1992, 33(A), 823–827; FEMS Microbiology Reviews 1992, 103, 299–310; TAPPI Journal 1993 May, 76(5), 71–77. From these it appears that the PHA, whether in the commercially obtained 21% or 27% V latex or in latex made by the hypochlorite route, was 95% pure and the latex particles invariably comprised an amorphous core within a crystalline shell. Experiments using the latex in making films are described and the suggestion is made to use it as a binder, coating material or barrier for paper or non-wovens. In patent application WO 91/13207 (corresponding U.S. Pat. No. 5,451,456) of the same author along with co-inventors the use of the 21% V latex in the production of the film and coated paper is described in more detail and a content of amorphous polymer is designated as essential.

Co-pending application WO 95/15260 describes a composite film made by applying partly amorphous, for example 34% crystalline, PHBV as latex to preformed cellulose film.

Co-pending application WO 94/07940 describes the preparation of a PHA suspension containing NPCM (non PHA cell material) decomposition products and surfactant, in which 60% of the PHA particles are amorphous (density 1.176) and 30% are crystalline (density 1.231), the remainder being non resolved in caesium chloride gradient solution. No means of removing the dissolved materials from the suspension is disclosed.

In each of the above prior documents the PHA may be 'virgin', that is, the product of solubilising and removing NPCM leaving the PHA particles as laid down in microorganism cells or as agglomerates thereof. (Whereas it is possible to make a latex by dissolving PHA in a volatile liquid such as chloroform, emulsifying the solution in water and removing the volatile liquid e.g. by evaporation, the PHA particles of such a latex are not virgin).

We have now prepared latex in which the suspended particles are of higher amorphous content. Such a latex has interesting properties for example substantial advantages when used in conjunction with film, paper or non-wovens, the advantages lying in the quality of the products and/or the convenience of the procedure used in making them.

The invention in its first aspect provides an aqueous latex of microobiologically produced PHA comprising virgin disperse phase particles of which fewer than 30, especially fewer than 20, especially fewer than 1, % w/w are crystalline.

Percentage crystallinity is as measured by density, X-ray diffraction or small or wide angle x-ray scattering (SAXS or WAXS). The percentages are by weight and are believed to represent:

$$\frac{\text{weight of crystalline PHA}}{\text{total weight of PHA in sample}} \times 100$$

where each particle is either wholly amorphous or at its maximum attainable crystallinity.

The particles of PHA are of weight average diameter (d 50) preferably under 5 $\mu$m, for example in the range 0.05 to 1.5 $\mu$m. Latex having particles of weight average diameter in the range 0.4 to 1.1 especially 0.5 to 1.1, $\mu$m is preferably the product of the process described hereinafter as the fourth aspect of the invention. Latex having particles of weight average diameter in the range 0.05 to 0.5 especially 0.1 to 0.4 $\mu$m is suitably the product of the process described hereinafter as the third and fourth aspect of the invention.

Suitable PHAs comprise repeating units of formula I:

$$-O-C_mH_n-CO- \qquad \text{I}$$

where m is in the range 1–13 and n is 2 m or (except when m is unity) 2 m–2. Typically $C_mH_n$ contains 2–5 carbon atoms in the polymer chain and the remainder (if any) in a side chain. In very suitable PHAs m is 3 or 4, n is 2 m and especially there are units with m=3 and m=4 copolymerised together with respectively a $C_1$ and $C_2$ side chain on the carbon next to oxygen. The molecular weight of the PHA is for example over 50000, especially over 100000, up to eg $2 \times 10^6$.

PHA of formula (I) containing only m=3 units is referred to as PHB; PHA containing m=3 and m=4 units is the co-polymer PHBV. The PHBV preferably contains 4–50, especially 4–30 and more especially 10–30 for example 12–25, mol % of m=4 units. The PHA can also be a blend of two or more differing in the value of m. A particular example contains:

(a) PHA consisting essentially of Formula I units in which 2–5 mol % of units have m=4, the rest m=3; and
(b) PHA consisting essentially of Formula I units in which 15–30 mol % of units have m=4, the rest m=3. The proportions in such a blend are preferably such as give an average m=4 content in the range 12–25%. To arrive at such blends, latices differing in m=3 and m=4 content, or precursors thereof, are mixed. However, it is preferred to use single polymers or blends of polymers all within the m=4 range 10–30 mol %.

The PHA is the product of a microbiological process in which the microorganism may be wild or mutated or may have had the necessary genetic material introduced into it. Alternatively the necessary genetic material may be harboured by a eucaryote, to effect the microbiological process. Microbiologically produced PHA is chiral (R) and stereospecific.

Examples of suitable microbiological processes are the following:

for Formula I material with m=3 or m=partly 3, partly 4:
   EP-A-69497 (*Alcaligenes eutrophus*);
for Formula I materials with m=3;
   U.S. Pat. No. 4,101,533 (*A. eutrophus*), EP-A-144017 (*A. latus*);
for Formula I material with m=7–13: EP-A-0392687 (various Pseudomonas).

Usually such processes include a cell growth stage followed by a PHA-accumulation stage: in the latter, an assimilable carbon source is provided, but the concentration of one or more nutrients essential to cell growth is limited or maintained at substantially zero. Such nutrients are conveniently one or more of nitrogen, phosphorus, sulphur or magnesium. The latex according to the invention is preferably the product of accumulation under limitation or absence of phosphorus.

The PHA is then separated from the PHA-containing cells by a harvesting process as described further below.

The polymer content of the latex is, in total if more than one is present, in the range 10–60, especially 20–50,% w/w.

The latex preferably contains a stabilising quantity of a surfactant other than NPCM.

The stabilising quantity of surfactant is typically in the range 0.25 to 10, especially 1 to 7% w/w on PHA dry solids. This is or includes surfactant in the latex after all steps of NPCM removal have been complete, including the final step of removing soluble NPCM decomposition products and unadsorbed surfactant. Thus it may correspond to a monolayer on the surface of the PHA particles, so far as this can be inferred from the sizes and shapes of the particles. Typically this quantity is the residue after washing of the surfactant used in a process according to the fourth aspect of the invention.

The surfactant can be anionic, cationic, non-ionic, zwitterionic or contain hydrophilic groups of more than one type. The hydrophilic part of the surfactant preferably contains at least 8, especially 12–20, carbon atoms per hydrophilic group. It may be (almost) wholly aromatic as in sulphonated naphthalenes and naphthyl methanes; or partly aromatic as in alkyl benzene sulphonates or ethoxylates; or wholly aliphatic. Very suitably the surfactant contains a linear alkyl group. If the surfactant is cationic, preferably its hydrophilic part is quaternary ammonium, based for example on tri $C_1$–$C_4$ alkylammonium. If it is anionic, the hydrophilic group is typically sulphate, sulphonate, carboxylate, phosphate or phosphonate. If it is non-ionic, it may be for example an ethoxylate, for example, an alkyl ethoxylate containing 7 to 16 (especially 12 to 16) alkyl carbons and up to 100 (especially about 20) ethoxylate units, or a block copolymer of ethylene oxide and propylene oxide or an alkylphenyl-ethoxylate (especially nonyl phenol with about 30 ethoxylate units). Suitable cationic surfactants include, typically as chloride or bromide: dodecyl-, tetradecyl- and cetyltrimethyl-ammonium, cetyldimethyl-ethylammonium, dodecyl-, tetradecyl- and hexadecyl-benzyldimethylammonium, benzalkonium, benzethonium, methylbenzethonium and cetylpyridinium. Suitable anionics include, typically as sodium or ammonium salts: dodecyl sulphate, N-lauroyl-sarcosinate, dioctyl-sulfosuccinate, cholate, deoxycholate, laurate, myristate, palmitate, and stearate. Suitable non-ionics include sorbitan monopalmitate, alkylglucosides and nonyl phenyl-ethoxylates. The cationic preferred is cetyltrimethyl-ammonium bromide. Sodium or ammonium deoxycholate, dodecyl sulphate, N-lauroylsarcosinate and dioctylsulfo-succinate are preferred as anionics. Ammonium forms of the anionics are preferred when it is desired to avoid introducing mineral matter.

Instead of or in addition to using such surfactant, the latex may contain an agent providing steric stabilisation, for example at least one water-soluble copolymeric dispersant containing a plurality—at least 2 and typically at least 10 and up to e.g. several hundred—of repeating units, including units of two types:
A PHA-compatible; and
B hydrophilic.

Such stabilisation is the subject of our co-pending GB application 9525390.2 filed Dec. 12, 1995.

Type A units may be for example aliphatic hydrocarbon (for example as in addition polymers) or aromatic hydrocarbon or (in chain lengths sufficient to give water-insolubility in a corresponding polymer consisting of such units) polyoxyalkylene, especially poly-1,2-propylene oxide or polyester of the head-to-tail or heat-to-tail/tail-to-head types such as for example, 12-hydroxy stearic acid polycondensate or alkyd resin. Preferably type A units carry substituents such as esterified carboxy groups or esterified or etherified hydroxy groups or both, since these afford greater compatibility with the PHA and are characteristic of compounds effective as plasticisers for PHA. Particular examples of such substituents are disclosed below for latex addition polymers as in the above-mentioned surfactants, and there may be hydrophilic groups of more than one chemical composition or ionic category. Very suitably it is polyethyleneoxy, especially 10 to 100 ethylene oxide units long, as is typical of conventional water-soluble surfactants.

The dispersant may contain a minor proportion for example under 20 mol percent, of units falling into neither type A nor type B.

The balance of type A and type B units should be such as to provide the water solubility, which typically is at least 1% w/w in water at 20° C. Preferably the type B units are in a minority by moles, for example less than one-third of the total chain units in the copolymer chain; correspondingly the water-soluble portion of the type B units, if polyethyleneoxy, should be sufficiently long. The HLB number (HLB signifies hydrophile-lipophile balance rating) of the dispersant is suitably in the range 10–15. Generally the dispersant is preferably from the class of non-ionic emulsifiers.

The latex may be formulated with additives such as:
(a) further, possibly different, surfactant;
(b) water soluble polymer as thickener and/or stabiliser, for example, cellulose ethers, vinyl or acrylic polymers, xanthan gum and associative thickeners eg based on urethane, acrylic or cellulose polymers;
(c) biocides, for example, 1,2-benzisothiazoline-3-one;
(d) co-solvents, for example, partly esterified or partly etherified glycols;
(e) pigment and/or pigment dispersant;
(f) one or more plasticisers;
(g) inorganic filler, for example glass fibre, carbon fibre, platy or foil particle, silica, clay, magnesium silicate;
(h) organic filler, for example cellulose fibre or particulate, protein fibre, synthetic polymer particle or fibre, wood flour;
(i) latex of polymer other than PHA for example as described below.

The latex is preferably substantially free of trace nutrient cations, for example those of manganese, iron, copper and zinc. It is also preferably very low in other soluble salts, other than the counter-ions of surfactants. Very suitably it is the product of a process in presence of a chelator.

The invention provides also a mixture of the above-defined latex with other latices, for example a different PHA or of a wax or natural addition polymers such as rubber or synthetic polymers such as PVC, PVDC, SBR, polyvinyl-acetate and polyacrylic esters as hereinafter defined. Further details are given hereinafter, in the sixth aspect of the invention. A particular mixed latex is binodal in particle size distribution especially with one maximum at about 0.21 $\mu$m and another at about 1 $\mu$m. The relative proportions may be such that the small particles substantially fill voids between the large ones, when the latex is subjected to coalescence.

The invention provides a harvesting process for making the latex from a suspension of microbiological cells containing the PHA by the steps of oxidatively solubilising at least partly the NPCM and applying to the resulting PHA particles a stabilising quantity of surfactant before the PHA has crystallised to the extent specified.

In this process the NPCM is solubilised leaving PHA of high purity, preferably at least 96, especially at least 98, % w/w. The harvesting process preferably includes a step of NPCM decomposition oxidation by peroxide in presence of a chelator and a surfactant, as described hereinafter as the third and fourth aspects of the invention.

Whichever sequence of steps is used in making the PHA virgin latex, any suspension that has undergone any NPCM attack should not be stored for more than a few days before receiving surfactant or undergoing oxidation. For example 7 days' storage of such a suspension has been observed to effect a halving of amorphous content.

Further precautions desirable for avoidance of crystallisation include keeping the suspension at a low ionic strength, keeping the suspension aseptic, not using hypochlorite and keeping the suspension within 2 pH units of neutrality. To keep down the ionic strength the production of the biomass is preferably in chemostat conditions maintaining the pH by addition of alkali in response to electrochemical measurement.

The invention in its second aspect provides a process of coating a substrate, more particularly making a water resistant structure, by applying to a water-sensitive substrate an aqueous PHA latex according to the first aspect. (The first aspect has been defined to include preferred latices and mixtures described hereinafter and the product of processes so described).

The substrate comprises at least sufficient water-sensitive material to be disintegrable in presence of water, whether liquid or vapour, without or with the action of acid, alkali or microbiology. In the first, simplest, case it consists of material soluble in liquid water: examples are non-polymeric substances, water-soluble cellulose ethers, polyvinyl alcohols, (possibly partly acetylated) and starch including foamed starch. In a second case it consists of materials swollen by water but not dissolved; examples are regenerated cellulose and incompletely acetylated celluloses. In a third case it consists of elements, such as fibres or plates or granules, bound together by such soluble or swellable materials or by inorganics such as alkali silicate. In a fourth case the substrate may consist of or be bound together by a biodegradable polymer such as a microbiologically produced polymer (eg PHA for rapid degradation) or a synthetic (e.g. polylactide or polycaprolactone for moderately rapid degradation).

Particular examples of the first and second cases are cereals and cereal products (especially breakfast cereals and wafers), sugar, sugar confections (especially chocolate), fruit (for example dried fruit especially raisins), meat and fish (raw, preserved or cooked), and also chemicals or medicines. Water insoluble packages for materials in these cases may be improved e.g. in moisture exclusion, by a coating of PHAs and/or mixtures described herein.

Particular examples of the third case are paper, fibre board and non-wovens. The invention is especially applicable to these, since it can afford a moisture barrier without rendering the coated material non-disposable by composting. Articles of this case include packaging sheets and containers, personal hygiene products, waste disposal bags and films for agriculture or horticulture. In view of the high gloss attainable, articles of good customer appeal can be produced, especially for food service crockery, including fast food packages and insulating packages. When used as a binder for fibres such as the cellulose fibres of paper or non-wovens, the PHA affords a substantial increase in mechanical strength. This property has not been observed using latices of PHA of a higher level of crystallinity.

Materials of the third and fourth case can be subjected to a degree of biodegradation and/or hydrolysis sufficient to permit re-use of at leasst part thereof. For example a PHA coating, possibly as a component of printing ink on fibre board can be biodegraded or solubilised and the board binders softened or dissolved sufficiently to permit pulping such as in a beater machine.

The latex may be applied to the substrate for example by dipping, spraying, doctoring, gravure-roll coating or reverse-roll coating. The application may be continuous over the surface, or through the interstices, of the substrate: if desired, it may be patterned, for a decorative effect or to effect a differential rate of biodegradation for example as between areas having PHA and uncoated areas, or with thickly coated areas alternating with thinly coated areas. Whichever application method is used, it is preferably controlled so that the applied particles are at least partly amorphous, although they may be less so than in the latex.

After application, the particles may be treated to effect coalescence. This can be effected by exposure to solvent vapour. Preferably it is effected by heating, for example in hot gas or in contact with a hot surface such as a calender-roll or by radiation such as microwave or infra-red. The temperature need not be high enough to melt the PHA. Preferably the heating to effect coalescence is applied to the latex carrying substrate while still wet, that is, while the latex component still contains water to the extent of at least 20 especially at least 50% w/w on the PHA. Thus drying and coalescence take place in a single step. For such a single step infra red heating is especially suitable. The single step of drying+coalescence can be effected in 10 to 20 seconds. This makes possible a continuous process of passing a continuous web substrate or continuous succession of substrate pieces through an application zone followed by an infra-red heating zone, with little or no drying between the zones and with infra-red input adjusted to complete drying and coalescence in a residence time under 30 seconds.

Whereas in general coalescence of the latex particles is affected by heating in preference to the action of solvent vapour, the heat input required can be less and the operating temperature lower than when using latex having a substantial content of crystalline or part crystalline PHA. When the particles are of average diameter less than 0.7 $\mu$m, e.g. in the lower ranges herein, heat input need be little more than, e.g. up to 150% of the latent heat of evaporation of the water of the applied latex coating. As a result, good coalescence is obtained in latex coating with drying at ambient temperature (15–25° C.). For more rapid processing, the temperature can be up to 50° C. or even 100° C. or the coated substrate can be dried at reduced pressure. The effect of using such small-particle latex is thus to permit the use of low-grade heat sources and/or the coating of temperature sensitive substrates. Such low-temperature processing is available whether the latex is virgin, as described elsewhere in this specification, or is in the product of dissolving the PHA in a water-immiscible liquid such as chloroform or 1,2-dichloroethane, emulsifying the resulting solution in water and removing the liquid, or of dispersing PHA in water as a melt or a solution in a water-soluble liquid.

Accordingly, as a modification of the second aspect a process of coating a substrate, e.g. for making a water resistant structure by applying a PHA latex thereto is characterised by using a latex in which the PHA particles are of average particle diameter up to 0.7 $\mu$m and drying the resulting coated substrate with a heat input little more than the latent heat of evaporation of the water applied in the latex.

Apart from the particle diameter and heat input features, the preferred conditions for this process are as described elsewhere herein.

Preferred products of the process or the modification thereof include paper and board carrying a glossy PHA coating, whether or not calendered, especially those characterised by the features:

(a) cellulose fibre paper or board substrate 20 to 600 g per $m^2$;
(b) PHBV (0 to 30 mol % V) coating, 0.5 to 30 $\mu$m dry thickness;
(c) gloss value 65–100, especially 70–75% at 60 degree incident light angle.

These values are substantially equal to those obtained by melt-coating the PHA. Such paper or board may carry the PHA layer on one or both sides.

The invention provides a fabric construct such as a paper or non-woven fabric having a PHA latex in its interstices and a construct of high mechanical strength made by heating such a construct so as to crystalline the PHA. The PHA latex is preferably as herein described.

The latex is also useful as a constituent of aqueous compositions to be applied to non-absorbent surfaces.

The invention in its third aspect relates to a process for recovering PHA in latex form from the cells in which it is accumulated.

Separation of PHA from NPCM has presented a long-standing problem. Extraction by solvent is inconvenient because of the high viscosity of the PHA solution and the expense of solvent recovery; it also requires complicated further processing steps if fine particles of PHA are required. Chemical treatment of the NPCM has been operated industrially but is susceptible of improvement to control the particle size of the PHA and/or its purity.

In an early proposal (Williamson et al. J Gen. Microbiol. 1958, 19, 198–203) the NPCM was solubilised by reaction with hypochlorite; however, this was accompanied by a serious loss in PHA molecular weight, for example from $10^6$ to $1.01 \times 10^{5}$ (See EP-A-145233, Example 18). Refined forms of hypochlorite treatment have been proposed (Ramsay et al. Biotechnology Techniques 1989, 3 (4), 227–232; 1990, 4, 221–226 and U.S. Pat. No. 5,110,980), but process conditions are narrowly described and appear to require extremely careful control to obtain high PHA purity without serious loss of yield or decrease of molecular weight. Neither of these references discloses the production of a latex or of material having a low degree of crystallinity.

Other oxidative treatments of NPCM have been proposed. According to EP-A-145233 the PHA containing cells are subjected to heat-shock and enzyme action and the resulting product is treated with hydrogen peroxide. According to application WO 94/24302 the efficiency of oxidative treatments of NPCM is decreased by side reactions catalysed by traces of the transition metal compounds added as nutrients in growing the microorganism cells in which the PHA is laid down. Therefore it is proposed to carry out the oxidative treatment in presence of a chelator. According to Examples 1–4 of that application, a PHBV purity of 99.5% is obtained by treating PHA-containing cells with hydrogen peroxide and a chelator. According to Example 4 the cells need not be the preliminarily heat shocked or enzyme-treated. The product of the oxidation treatment is processed to dry PHA.

A further expedient proposed for NPCM removal is treatment with a surfactant. For example in Example 5 of EP-A-145233 it is reported that PHB made by boiling cell suspension at 100° C. for 60 min was 72% pure in absence of added surfactant but 93% pure in presence of sodium dodecyl sulphate (SDS) 10% on cell dry weight. In Ramsey et al (Biotechnology Techniques 1990, 4, 221–226 and U.S. Pat No. 5,110,980) it is disclosed that biomass that has been treated with anionic surfactant and separated therefrom is more fully freed of NPCM by hypochlorite digestion. In co-pending application WO 94/10289 it is disclosed that PHA bearing cells were treated with SDS and hydrogen peroxide for 16 hours at room temperature, washed and treated with hydrogen peroxide at 80° C. for 3 hours; the resulting PHA was at least 99% pure. However, the product PHA was processed to dry polymer.

Much work has been done on enzymatic degradation of NPCM. Thus in EP-A-145233 a proteolytic enzyme, such as "Alcalase", "Protease", "Neutrase", "Esparase", "Allprotease" or "High T" (all believed to be registered trade marks) or bromelain or papain and/or combinations of two or more of these, were applied to cells following a "heat-shock" treatment at 80–200° C.; the product of such proteolysis may be subjected to a phospholipase enzyme for example "Lecitase" or to other enzymes exemplified by lysozyme and "Novozyme" (RTM). WO 94/07940 describes the preparation by the succession of heat shock, then protease, then surfactant+hydrogen peroxide of a PHA suspension in which 60% of disperse phase particles are amorphous, 30% are crystalline and 10% were not resolved. These particles have a mean diameter (d 50) of 0.98 $\mu$m.

A latex of virgin PHA particles of d 50 weight average diameter mainly or wholly in the range 0.05 to 0.5 $\mu$m, and mainly or wholly amorphous has now been produced. It has valuable properties such as rapid coalescence when used to produce films or coatings.

According to the invention in its third aspect an aqueous latex comprises PHA in the form of substantially amorphous wet virgin particles that are single or agglomerates of up to 25 single particles. The particles are of average diameter d 50 in the range 0.05 to 0.5, especially 0.1 to 0.4, $\mu$m and preferably are substantially free of contamination by alkali metal ions or halogen ions or organic halogen or chelatable metal ions. They are preferably less than 30, preferably less than 20 and especially less than 1, percent crystalline, measured as hereinbefore described.

By "single" is meant the particles as they existed within the cell walls of the microorganisms in which they were laid down. It appears that within the walls of each cell of the microorganisms listed above, especially those mentioned below, the PHA is laid down discretely as a number—typically up to a few hundred, for example 10 to 25—of such particles. It is believed that the particles according to the invention are these single particles or intra-cell agglomerates thereof. Typically they contain less than 4, especially less than 2, % w/w of NPCM residues.

The latex may be the product of separating PHA from cells containing it by a harvesting process including NPCM solubilisation by peroxide in the presence of a chelator and a surfactant, especially as described below.

The surfactant may be present as a result of use in separating NPCM, but there may be present instead or in addition, stabilisers such as other surfactants and/or water-soluble polymers. Examples of these and other additives are set out above.

The concentration of PHA in the latex is typically 100 to 600, especially 200 to 500, g/l.

The concentration of surfactant in the latex is as described for the first aspect of the invention.

The invention also includes a latex precursor, that is, before separation of some or all of the NPCM decomposition products and unadsorbed surfactant if present. Typically the surfactant concentration in such a latex precursor is in the upper two-thirds of the ranges mentioned above.

In its fourth aspect the invention provides a process for making PHA by producing by fermentation a biomass of microorganism cells containing PHA and harvesting PHA by decomposing NPCM by steps including treatment with a surfactant and an oxidant: characterised in that the said treatment is applied to the biomass before substantial (as hereinafter defined) decomposition of the NPCM by other means.

A preferred process is characterised further in that the biomass to which the treatment is applied is the product of fermentation under phosphorus limitation.

The treatment is applied to the biomass preferably without significant dilution or concentration (that is, by a factor of more than 2), conveniently to whole fermentation product, which typically contains 100–200 g/l of cells (dry weight excluding PHA) the cells containing 50–80, especially 65–75, % w/w of PHA.

The oxidant is preferably one that at pH levels up to 1 unit above or below neutrality is stable against side reactions. It is preferably a peroxide, especially hydrogen peroxide and preferably a chelating agent is present, for example an amino polycarboxylic acid such as ethylenediamine tetra acetic acid or a nitriloacetic acid, a hydroxy polycarboxylic acid such as citric acid or tartaric acid; an amino polyphosphonic acid such as diethylene triamine penta methylene phosphonic acid (DTPA); or a polyphosphate such as tripolyphosphate. Each is of course present as a salt corresponding to the pH to which the mixture is adjusted. The temperature of the oxidation step is suitably in the range 50–90° C. and this is typically maintained for 6–24 h.

The surfactant can be any of those listed above; if two or more are used together, these should normally not include both a cationic and an anionic. The content of surfactant during this step is suitably in the range 0.2 to 10, especially 1 to 5, % w/w on dry PHA solids.

Preferably the oxidant, chelator and surfactant are present together for at least the bulk of the reaction time. Preferably the chelator and oxidant added are before the surfactant, or before the temperature is raised to 50° C. or above: thus surfactant may be present as the result of a pre-treatment at under 50° C., as described further below. To limit side reactions, the chelator is preferably added before the oxidant. The temperature and time can be in the same range as defined above for the oxidation step.

The harvesting process normally includes separation of PHA from soluble NPCM decomposition products; this step also separates surfactant. When PHA is to be recovered as a latex the quantity thereof used for solubilising NPCM is preferably greater than the quantity needed to stabilise the latex. In the separation step it is important to avoid mechanical treatments sedimenting or compressing the particles together or otherwise injuring them. This is the subject of the fifth aspect of the invention.

By "substantial decomposition" of the NPCM is meant over 50% w/w solubilisation of more than one of three major components of NPCM, namely protein, nucleic acid and peptido-glycan. If a treatment step before the claimed surfactant and oxidant treatment is used, it is preferably at not over 50° C., for example:
(a) mechanical homogenisation suitably at high pressure using for example a French pressure cell and possibly in presence of surfactant;
(b) oxidant/surfactant depolymerisation of nucleic acid; or
(c) enzyme digestion to solubilise peptido-glycan by a cell wall lytic enzyme such as lysozyme. In general the process may include other steps previously proposed for such harvesting, for example heat-shocking the cells, cell wall breaking by audible sound, ultra-sound or high pressure homogenisation or even freeze-drying providing that substantial crystallisation or agglomeration is not provoked thereby.

The step of cell wall disruption by mechanical means in presence of surfactant is of more general application and constitutes a further aspect of the invention.

Whereas the invention in the fourth aspect is primarily concerned with a latex and latex-making process, it may include the further step of converting the treated biomass or the latex to larger PHA particles or (via such particles or direct) to dry PHA. The surfactant should be of such a kind or in such a concentration that the properties of articles to be made are not impaired.

Conversion to larger PHA particles is conveniently effected by heating, as described in co-pending Application WO 94/02622. Conversion to dry PHA can be effected by spray-drying. Other preferred methods, including freezing, freeze-drying or flaking, also produce particles of high accessible surface, so that excess surfactant or stabilising colloid can be removed by washing. Such conversion can be carried out in conditions gentle enough to avoid gross crystallisation of the PHA; this of course is not critical if subsequent solution- or melt-processing is intended.

The PHA can be used in any of the usual methods for forming shaped articles from dry polymers, for example, injection moulding, extrusion including co-extrusion with other polymer, spinning or coating onto substrate.

The fifth aspect of the invention arises from the observation that many procedures for removing such dissolved materials, for example bowl centrifugation or filtration, provoke a substantial increase in crystallinity.

According to the fifth aspect of the invention a process for producing a PHA latex of substantial amorphous content comprises:
(a) forming a biomass containing micro-organism cells containing PHA particles;
(b) decomposing the non-PHA cell material of the cells to soluble products;
(c) separating the soluble products from the PHA particles; and
(d) forming an aqueous dispersion of PHA particles substantially free of such soluble products; and is characterised by:
carrying out step (c) by resolving the product of step (b) into a solution of the soluble products and a non shear-thickening slurry.

The slurry is flowable and contains preferably not more that 50, for example in the range 10–40,% w/w of PHA particles.

Such resolution distinguishes particularly from conventional filtration in which filtrate is squeezed from a wet filter cake, or conventional centrifugation in which a static pellet or layer is formed and subjected to enhanced gravity to remove liquid; such conventional procedures typically also include mechanical working to effect redispersion in aid of further washing or to produce a latex. The process of the invention is preferably carried out without, or with at most transient or localised, formation of paste more concentrated than the stated limits.

Step (b) may include initial stages possibly in absence of added surfactant. These stages typically include one or more of:
heat-shock, that is, a rapid temperature rise to 80–200° C. effected for example by injection of high pressure steam;
enzyme treatment by hydrolase such as lysozyme to decompose peptido glycan;
enzyme treatment by a proteolytic enzyme to decompose cell wall protein,
cell wall breaking by audible or ultra-sound;
high pressure homogenisation;
oxidation.

In one preferred form of the process, step (b) is carried out by the process of the fourth aspect of the invention.

A process including one or more of such stages to decompose 80 to 90% of NPCM, followed by oxidation in presence of surfactant to remove most or all of the remaining NPCM, characteristically produces particles of mean diameter in the range 0.4 to 1.5, especially 0.75–1.05 $\mu$m; by the use of the invention they can be under 30, especially under 20, for example under 1, % w/w crystalline.

In either form of the process the solubilisation of NPCM is conducted so as to produce PHA preferably at least 96, especially at least 98, % pure.

The surfactant can be any of those listed above; if two or more are used together, these should normally not include both a cationic and an anionic. The content of surfactant during step (b) is suitably in the range 0.2 to 10, especially 1 to 7, % w/w on dry PHA solids.

If desired, there may be a treatment such as mechanical treatment in presence of surfactant or a lysozyme digestion or a surfactant/oxidation step to decompose nucleic acids, thus decreasing the viscosity, in each case at a temperature in the range 15–50° C.

Separation step (c) can be carried out by any method, provided the product slurry concentration remains within the stated ranges. Decantation can be used without special precautions. Thus, if centrifugation is used, the g-value and residence time are adjusted so that the residue is a paste, rather than a pellet; conveniently a continuous centrifuge is used. Washing by decantation can be used, alone or as a preliminary to a different method.

A preferred method of separation involves tangential flow filtration. This is described for example in the article by Redkar and Davis (Biotechnol.Prog. 1933, 9, 625–634). It involves contacting the suspension under pressure with a membrane of predetermined pore size (suitably $10^5$ molecular weight cut off to 0.1 $\mu$m for the process of the invention); preferably the suspension is caused to flow along the surface of the membrane to exert a shear. Since a static filter cake does not build up, there is little if any compression of the particles and thus agglomeration and crystallisation are minimised.

A preferred method of separation comprises:
(a) flowing the latex transversely of one side (the upstream side) of a membrane permeable to solutes but impermeable to latex particles, at a flow rate setting up a shear maintaining the PHA particles of the latex in suspension;
(b) taking an aqueous solution of the solutes from the other side (the downstream side) of the membrane;
(c) adding further water to the suspension whereby to effect further removal of solutes from the suspension.

The relative rates of solution off-take in (b) and water addition in (c) may be controlled to effect a net dilution or concentration of the starting latex. The added water may contain other materials, for example surfactant, if it is desired to maintain the presence of such material in the resolved latex. Preferably the liquid at the upstream side of the membrane is maintained at a hydrostatic pressure higher than at the downstream side. In this method, since a static filter cake does not build up, there is little if any compression causing mutual collision of the particles and thus agglomeration and crystallisation provoking events are minimised.

If the process includes other steps previously proposed for such harvesting, for example heat-shocking the cells, cell wall breaking by audible sound, ultra-sound or high pressure homogenisation or enzyme digestion, or even freeze-drying, these should be in conditions such that substantial crystallisation or agglomeration is not provoked.

It has been found that substantial advantages accrue when latices of a defined class are used in conjunction with the latex described hereinbefore.

According to the invention in its sixth aspect there is provided a mixture of at least one PHA latex (first latex), at least part of which is according to the first aspect of the invention, with at least one latex (second latex) of a polymer other than the PHA and preferably compatible with the PHA, at least when at the low crystallinity levels herein-before described.

The said polymer may be a condensation polymer or an addition polymer. Such an addition polymer may have at least one of the following characteristics:
average particle diameter in the range 10 to 1000, especially 20 to 500, more especially 50 to 100 nm;
surfactant concentration less than 3, especially less than 2, for example in the range 0.2 to 1.5%, w/w on total solids;
at least one-third, especially at least one-half, by moles of its repeating ethylene-residue units carrying direct or through CO at least one oxygen-linked hydrocarbon group of 2 or more carbon atoms.

The particle diameter of the second latex is preferably less than, for example 0.001 to 0.1 or up to 0.5 times that of the first latex.

The surfactant concentration of the second latex is preferably less than that of the first latex. It is believed that, on mixing the two latices, the second latex may take up from the liquid phase of the first latex, surfactant, leaving the first latex less tending the shear-thickening or flocculation.

The oxygen-linked residues carry ester or ether groups. Examples of ester groups are (a) those of the acids acrylic (as hereinafter defined), maleic, fumaric and itaconic, with $C_{2-18}$ alcohols and phenols; (b) those of allyl alcohol or the notional vinyl alcohol with $C_{2-18}$ carboxylic acids. Examples of ether groups are those of allyl alcohol or the notional vinyl alcohol with $C_{2-18}$ alcohols and phenols. Such alcohols and carboxylic acids can be straight-chain, branched or cyclic but, if substituted, do not include groups conferring water-solubility on the polymer in the proportion used.

The balance of the units in the second latex polymer can be for example one or more of ethylene, propylene, styrene (preferred), vinyl halides, vinylidene halides, vinyl methyl ether, acrylic (as hereinafter defined) nitrile or methyl ester and conjugated olefins. Hydrophilic groups such as carboxylic acid or amide should be at too low a concentration to confer water-solubility, typically under 10 mol %.

The term 'acrylic' is hereby defined by the general formula:

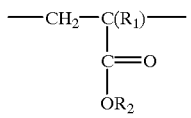

where $R_1$ is hydrogen, $C_{1-12}$ alkyl (especially methyl), cycloalkyl, aryl, halogen or cyano and $R_2$ is a $C_{2-18}$ hydrocarbon group. The analogous definition applies to the corresponding nitrile if present.

The condensation polymer is suitably a polyester or polyurethane.

According to the invention in its seventh aspect a process of making a water resistant structure comprises applying to a water sensitive substrate mixture of the said first and second latices.

The first latex may contain crystalline PHA particles but preferably the extent of crystallinity is low, as hereinbefore described. It preferably contains only virgin particles, that is, the product of forming PHA microbiologically as a cell constituent, then solubilising and removing non-PHA cell material (NPCM) leaving the PHA particles as laid down in microorganism cells or as agglomerates thereof. Alternatively the first latex may be wholly or partly the product of emulsification, that is, dissolving PHA in a volatile liquid such as chloroform, methylene, chloride or 1,2-dichloroethane, emulsifying the solution in water and removing the volatile liquid e.g. by evaporation or diffusion, as described in co-pending application WO 94/07940. When the first latex is the product of emulsification, the PHA can be wholly or partly synthetic, as made for example by the processes of Bloembergen et al., Macromolecules 1989, 22, 1656–1669.

Other preferred forms of the first latex are as described in co-pending application WO 94/07940, subject to the requirement that any surfactant to be present should be chosen for compatibility with the addition polymer latex.

The first latex may be made from a solution of PHA in a liquid having substantial solubility in water, for example an alkylene carbonate.

The polymer of the second latex preferably has a film forming capability at temperatures up to 20° C. for example in the range minus 20 to +60° C., especially 0– 20° C. This polymer is preferably at least a terpolymer. Preferably no one unit of the four mentioned is present at over 50% w/w. The over-all balance of units is preferably such as to provide amorphous resins in the "hydrophobic" class; thus at least one of its monomers is itself substantially insoluble in water. The second latex is typically the product of emulsion polymerisation or dispersion polymerisation. An organic liquid may be present.

The second latex polymer is substantially amorphous. Its molecular weight is preferably over 50000, especially over 100000. Usually its molecular weight is not more than $5 \times 10^6$.

The repeating units are preferably selected from:
styrene;
acrylic esters having $C_3$–$C_{10}$ side chains; and
acrylic acid.

The acrylic acid is present preferably to the extent of 3–10% w/w. The (meth)acrylic ester is preferably a mixture of acrylic and methacrylic esters. The acrylic ester is preferably an octyl ester; the methacrylic ester is preferably a butyl ester.

The proportions of the repeating units are preferably in the ranges:
styrene x parts by weight
acrylic ester (0.7 to 1.3) x
methacrylic ester (1.5 to 2.0) x.

These relative proportions of the first and second latices can be chosen according to the intended use of the mixture and the technical effect desired. If the intended use is biodegradable-coated substrates, the proportion of second latex should be limited, for example up to 20% w/w on a dry solids basis, but can be higher for example in the range 20–80% w/w if biodisintegration is acceptable. If rapid biodegradability is not essential, higher contents of second latex for example up to 95% w/w can be used. The mixed latex is less liable to shear-thickening and/or flocculation than the PHA latex alone.

The second latex is typically the product of polymerising olefinically unsaturated monomers in presence of a free-radical-generating initiator with appropriate heating or irradiation in an aqueous medium with conventional dispersants. Such a latex could be used as such or isolated and redispersed. Typical dispersants are anionics such as Na, K or NH4 salts of $C_{12-20}$ carboxylic acids, dialkylsulphosuccinates, sulphated oils, alkane sulphonic acids, and alkyl sulphates and non-ionics such as exthoxylated fatty acids and/or amides. The dispersant can be of a type copolymerisable with the monomers. The amount used is usually 0.1 to 5% w/w on the total monomer(s) used. Typical initiators are hydrogen peroxide, persulphates and redox systems, generally at 0.05 to 3% w/w on the total monomers used.

EXAMPLE 1

COATING

Latices having the following properties were used:
solids content 35–40% w/w
disperse phase composition 84 HB/16 HV mol percent
molecular weight about 500000
particle size average 0.8–1 µm
percentage crystallinity under 1% by WAXS surfactant "Synperonic A20" (RTM), a condensate of $C_{12}$ alkanol with 20 mols of ethylene oxide.

These had been made by fermenting glucose and propionic acid with *Alcaligenes eutrophus* with phosphate limitation, then harvesting by steam injection, proteolytic enzyme action and digestion with chelator+hydrogen peroxide+surfactant added in that order; solubles and excess surfactant were then removed by membrane-flow filtration. This process is described more fully in Examples 6 and 7 hereinafter.

Coatings were made on the following substrates:
A cellulose fibre board 280 g m²; (Hermiboard BO16 from Cascades Blendecques SA)
B natural regenerated cellulose film 18 µm ("Cellophane");
C compression moulded starch.

Coating was by means of a large K hand coater (R K Print-Coat Instruments Limited, Royston UK) using a metering rod giving a 12 µm wet coat thickness. The coated substrates were dried in an air circulating oven at temperatures and for times set out in the tables below. Some were treated further by calendering at 130° C. through rollers. Other samples were dried or further treated by infra-red heating.

Test Methods

MVTR ("Moisture Vapour Transition Rate")
This was measured at 23° C., 85% RH (temperate) or 38° C. 90% RH (tropical) using a Lyssey L80 instrument calibrated daily against a standard PET film. The coated substrate samples were conditioned at room temperature for at least 24 h before starting MVTR measurement. Measurements were made at intervals until equilibrium was reached: the final 10 readings were averaged.

COBB test

Apparatus conforming to ASTM D2045-64T was used. In this apparatus a weighed coated board sample is clamped coating side upwards to the end of a metal cylinder and de-ionised water is poured into the cylinder. At 30 min the water is poured off and the sample is detached, wiped and weighed. The test was carried out at room temperature. The amount of water adsorbed is expressed in g per $m^2$.

GLOSS

A Microtry Gibbs instrument was used, with a 60 degree incident light angle.

Grease Resistance

This was determined by the "Kit Test" UM557 as described in 1991 TAPPI Useful Methods Page 175. In this test the test specimen is placed on a flat surface and dripped with each of 12 solutions of castor oil, toluene and heptane differing in composition so as to provide a gradation of aggressiveness to hydrophobic materials. Results are shown in the following Tables in which coating thicknesses are approximate.

TABLE 1

Effect of coating and drying conditions for board:

| Coating conditions $\mu$m wet | Coating thickness $\mu$m dry approx | Cobb values g/m² vs drying conditions | | |
|---|---|---|---|---|
| | | Oven 130 C. 10 min | Infra-red 10 sec | Infra-red 15 sec |
| 1 × 6 | 2.4 | 94 | 77 | 60 |
| 2 × 6 | 4.8 | 28 | 5 | 3 |
| 1 × 12 | 4.8 | 53 | 34 | 12 |
| 2 × 12 | 9.6 | 12 | 1 | 3 |

It is evident that two thin coatings are more effective than a single coating of double the thickness. Infra-red heating is both more effective and more rapid in giving an impermeable coating. The best products are equal to those obtained using non-biodegradable polymer coating for example:

| | Thickness dry, approx, $\mu$m | Cobb g/m² |
|---|---|---|
| Acrylic latex | 5 | 5 |
| Viclan (RTM) PVDC | 5 | 1 |

The samples whether calendered or infra-red heated showed a high level of gloss (70–75% at 60 degree light angle) and grease resistance (kit value 12/12; not affected by 90 toluene +100 heptane v/v mixture).

TABLE 2

MVTR : Comparison with melt coated board
(2 × 6 $\mu$m applications; 15 sec infra-red drying

| | Dry thickness $\mu$m | Cobb g/m² | Temperate MVTR g/m²/day |
|---|---|---|---|
| No Coating | 0 | 137 | 450 |
| 2 × 6 $\mu$m wet | 4.8 | 3 | 143 |
| melt coated | 6.2 | 5 | 150 |

It is evident that by using the specified latex and drying by infra-red, the level of moisture resistance is substantially equal to that obtained by melt coating.

TABLE 3

Water Vapour Transmission of Coated Cellulose Film

| Polymer, thickness $\mu$m (nominal) | | MVTR g/m² day$^{-1}$ | |
|---|---|---|---|
| | | Temperate | Tropical |
| | 0 | 735 | 1202 |
| PHBV | 4.4 | 148 | 764 |
| Acrylic | 4.8 | 179 | n/a |
| PVDC | 4.8 | 4 | n/a |

TABLE 4

Coated Starch Substrate: Cobb Test

| | Cobb Water transmission g/m² |
|---|---|
| Uncoated | 638 |
| PHBV 9% w/w | 516 |

EXAMPLE 2

Paper Binder

The same latex was used, but was diluted to 20% w/w for spraying on to the substrate. The substrate was an 80 g m$^{-2}$ air-laid non-bonded paper precursor. The latex was applied by aerosol spray to both sides of the substrate and flowed into the interstices of the paper. The resulting sheets were dried in an oven at 80° C. for 1 h.

Samples from the sheets were tested for peak-load at failure in these conditions.

Equipment: Instron Type 1122 tensile tester
Sample dimensions: 30 mm×10 mm
Number of replicates: 3, in each of 2 perpendicular directions per sample
Test Speed: 5 mm min$^{-1}$
Jaw Separation: 10 mm
Gauge Length: 10 mm
Full Scale Load: 20N
Results: The mean peak load (N) derived from the 6 tests was reported for each sample.

Results are shown in Table 5.

TABLE 5

| | PHBV % w/w | Mean Peak load at failure, N |
|---|---|---|
| Unbonded paper precursor | 0 | 0.9 |
| PHBV-bonded paper precursor | 16.5 | 1.90 |

This result is to be compared with those reported in the article by Marchessault et al. (TAPPI Journal, May 1993, 76(5), 71–77 at pages 73–74):

II Physical and mechanical characteristics of PHB and PHB/HV latex coated paper

| Characteristic | PHB | PHB/BV | Base stock |
|---|---|---|---|
| Basis weight g/m$^2$ | 48.0 | 74.0 | 37.4 |
| Burst index, kPa-m$^2$g | 0.90 | 1.65 | 2.31 |
| Breaking length, km | 4.75 | 5.10 | 6.85 |
| Stretch, % | 0.95 | 2.10 | 1.59 |
| Tensile index, N-m/g | 46.30 | 50.20 | 67.16 |

It is evident that the application of the partly crystalline latex used by these authors does not increase the tear strength of the paper.

EXAMPLE 3

(a) Coatings on paper were made using virgin latex of particle size 0.2 μm made by the process of the fourth aspect of the invention (Example 4 below), that is, by direct action of chelator and hydrogen peroxide and surfactant on the fermentation product described in Example 1. The particles of the latex contained under 2% w/w of NPCM residues and were less than 1% w/w crystalline.

The PRA layer was readily coalesced by moderate heating of the latex coating.

(b) Coatings on board (single application, 12 μm wet thickness) (See Example 1) were made using solvent-route* latices of average particle diameter in the range 0.1 to 0.5 μm and dried by various procedures. Table 6 shows the Cobb test results for these latices, with comparison results for larger particle virgin latices and for an acrylic latex.

TABLE 6

Effect of Particle Size on Cobb Performance

| | | Cobb/g m$^{-2}$ | | | |
|---|---|---|---|---|---|
| HV Level mol % | Particle Size μm | Oven 130° C. 3 min | IR 150° C. 15 min | Oven 80° C. 0.5 min | Room Temp. overnight |
| 16 | 0.1–0.2 | 9 | n.m. | 19 | 9 |
| 27 | 0.1 | 8 | 14 | 5 | 6 |
| 27 | 0.1–0.2 | 11 | n.m. | 12 | 8 |
| 23 | 1.4 | 108 | 18 | 150 | n.m. |
| 18 | 0.9 | 75 | 12 | 157 | n.m. |
| Acrylic | 0.08 | 6 | 8 | 6 | 6 | n.m. = not measured
*The solvent route consisted in dissolving the PHA in chloroform to give a 5% w/w solution, emulsifying the solution in aqueous sodium N-lauroylsarcosinate, removing the chloroform by warming at 65° C. in a current of nitrogen and adjusting surfactant to ca 5% on PHA. It is evident that, at particle diameters 0.2μ and under, overnight drying at room temperature is as effective as at higher temperatures.

EXAMPLE 4

Preparation of small-particle latex

In a stirred fed batch fermenter *Alcaligenes eutrophus* was grown on glucose as carbon source, then fermented with glucose and propionic acid under phosphorus starvation to effect accumulation of a PHA consisting of HB and HV units in the molar ratio 85:15.

To the fermenter product at ambient temperature sodium N-lauroylsarcosinate (6.5% w/w on the PHA) was added and mixed in. The mixture was passed once through a French pressure cell (105.6 kg/cm$^2$) to disrupt the cells, then adjusted to pH 6.8 by addition of 5M potassium hydroxide. Chelator DTPA (1% w/v), sodium hydrogen phosphates pH 6.8 and silicone antifoam (100 ppm w/v) were stirred in. The mixture was heated to 80° C. Hydrogen peroxide 60% w/v solution was added to provide 3% w/v $H_2O_2$ in the mixture. The mixture was stirred at 80° C. for 12 h, with a further hydrogen peroxide addition at 3.5 h to replenish the 3% w/v level, and with periodic adjustment of pH to 6.8. The mixture was then passed to a tangential flow filter in which soluble material was separated, leaving a stable latex of PHA content 400 g/l.

In the resulting latex the average particle size was 0.35 μm. The particles were examined by density measurement and found to be less than 1% w/w crystalline. The PHA contained less than 2% w/w of NPCM residues.

EXAMPLE 5

Fermenter contents prepared as in Example 4 were treated with lysozyme (0.1% on cell dry weight) at 25° C., pH 7.5 for 5 h. Then the treatment with chelator, hydrogen peroxide, and also surfactant (sodium N-lauroylsarcosinate) and antifoam, and subsequent work-up steps, were carried out as in Example 4.

The latex average particle size was 0.21 μm and the purity and crystallinity of the PHA were very similar to those of the latex of Example 4.

It is evident that the initial treatment at relatively low temperature has not led to aggregation of latex particles or to nucleation events provoking crystallisation.

EXAMPLE 6

Conditions for PRA Washing

In a stirred fed batch fermenter *Alcaligenes eutrophus* was grown on glucose as carbon source, then fermented with glucose and propionic acid under phosphorus starvation to effect PHBV accumulation. The contents of the fermenter were then fed through a wide tube into which high pressure steam was injected to partly disrupt the cells by heat shock. The resulting suspension was passed into a first reactor, where it received protease enzyme and was digested for a suitable period. The digested product, consisting mainly of PHA particles and soluble material, was separated in an intermittent or continuous centrifuge (A). The particles were washed with water, back washed to re-suspend them and passed into a second reactor, where they were stirred with chelator, hydrogen peroxide and surfactant (added in that order) until residual NPCM was substantially oxidised. The resulting suspension was passed into an intermittent or continuous centrifuge (B), which was powerful enough to deposit surfactant-coated PHA particles despite the presence of surfactant in solution. The deposit in the centrifuge was washed with water by suspension and further centrifugation and passed into a separator, which was an intermittent or continuous centrifuge or a membrane flow (MF) filter (C). Here residual soluble material was removed, leaving a stable latex.

Heat Shock pH 8.5;
  steam temperature 150° C.;
  residence time 80 sec;
First Reactor protease concentration 0.5% w/w.
  temperature 70° C., residence time 2 h;
Second Reactor pH 7.0,
  $H_2O_2$ 1.5% w/v, added as 35% w/w aq.soln;
  chelator 0.2% w/w DTPA;

surfactant 5.0% w/w,
anti-foam 0.05% w/w;
temperature 80° C., residence time 12 h;
MF-filter varied to give latex polyester concentrations over the range 10 to 40% w/w.

The effect of separator conditions on crystallinity, as shown by density measurement, is shown in Table 6.

TABLE 6

| Separator | Mechanical Design | PHA % w/w in product paste | Crystallinity |
|---|---|---|---|
| A | Intermittent Discharge Centrifuge | 25 | under 1 |
|   | Continuous Discharge Centrifuge | 25 | under 1 |
| B | Intermittent Discharge Centrifuge | 25 | 100 |
|   | Continuous Discharge Centrifuge | 25 | under 1 |
| C | Intermittent Discharge Centrifuge | 35 | 100 |
|   | Continuous Discharge Centrifuge | 25 | under 1 * |
|   | MF-filter | 40 | under 1 |

* If no solids retention

Using the continuous discharge centrifuge at B and the membrane flow filter at C, the following variations were examined.

The surfactants used in successive runs were:
Synperonic A20 (non-ionic: $C_{12}$ alcohol/20 EO)
Sodium lauryl sarcosinate (anionic). No significant difference was observed.

The effect of surfactant concentration was examined in the range 0.5 to 8.0% w/w on polymer solids: no difference in crystalline content of the polyester particles was observed.

The effect of the process on PHBVs of various V content was examined. At low V content (5% molar), the particles in the 40% w/w latex were more crystalline than those in less concentrated latices. At a given latex polymer concentration, namely at the end of reaction in the second reactor, a 18% V polyester was under 1% crystalline, compared with a 5% V polyester which was 10–15% crystalline.

In each of the runs the latex average particle size was 0.95 $\mu$ for 8% V or 20% V and 0.55 $\mu$ for 16% V. It is believed that these particles are agglomerates of part or all the single particles initially within cells but without polyester from other cells. The particles contained less than 2% w/w of NPCM residues.

EXAMPLE 7

The initial fermentation was carried out in Example 6.

The contents of the fermenter were fed to a reactor and hydrogen peroxide (4.0% w/v as 35% w/w solution), chelator as in Example 4, and surfactant (Synperonic A20: C12 linear alcohol 20 EO at 6% w/w) were added in that order, with stirring between additions. Silicone anti-foam (0.05% w/w) was also added. The pH was adjusted to 7.0 and the temperature at 80° C. The mixture was stirred until desorption and solubilisation of NPCM were complete (12 h), then passed to a membrane flow filter, in which soluble material was separated, leaving a stable latex of polymer content 40% w/w.

In the resulting latex the average particle size was 0.21 $\mu$m. The particles were examined by density measurement and found to be less than 1% w/w crystalline. They contained less than 2% w/w of NPCM residues.

EXAMPLE 8

PHA latex mixed with acrylic latex

The following starting materials were used:
PHA latex PHBV (23 mol % V) of Mw $1.14 \times 10^6$
  solids content 41% w/w
  PHA content of particles over 98% w/w
  particle size 1.3–1.5 $\mu$m (volume average)
  crystallinity under 5%
  surfactant 3 to 5% w/w on PHA dry solids
  origin: fermentation of *Alcaligenes eutrophus* with glucose and propionate in growth stage followed by phosphate-limited accumulation stage; harvesting by heat-shock, then digestion with enzyme, hydrogen peroxide and surfactant Second Latex (% w/w) styrene 25;
  2-ethylhexylacrylate 25;
  n-butylmethacrylate 43;
  methacrylic acid 7;
  molecular weight ca 150000
  minimum film forming temperature 15–17° C.
  solids content 40% w/w
  particle size 75–80 nm (0.0075 $\mu$m, substantially amorphous
  surfactant: sodium lauryl-sulphate
  pH 9.0.

Quantities of the two latices were blended to give PHA and acrylic in the ratio 100 to 15 as dry solids. It was noticed that the blend showed no signs of shear-thickening. The blend was coated on paper board samples at 12 $\mu$m wet thickness in one application by hand draw-down using Meyer k-type bars. This wet thickness corresponds to 4–5 $\mu$m dry thickness. The samples were dried by either of two methods, namely:

oven at 130° C. for 3 min; or infra-red at 150° C. for 15 sec.

(The 150° C. is the temperature measured at the paper surface). Five replicates of samples coated using the blend, and also of samples coated with 100% PHA latex or second latex were prepared and subjected to the Cobb test as described in Example 1. Results are shown in Table 7.

TABLE 7

| Latex Composition w/w | | Drying | |
|---|---|---|---|
| PHA | ACRYLIC | Method | Cobb g m$^{-2}$ |
| 100 | 0 | Oven 130° C. 3 min | 107 |
| 100 | 0 | IR 150° C. 15 sec | 27 |
| 100 | 15 | Oven 130° C. 3 min | 34 |
| 100 | 15 | IR 150° C. 15 sec | 19 |
| 0 | 100 | Oven 130° C. 3 min | 6 |
| 0 | 100 | IR 150° C. 15 sec | 8 |

Thus small addition levels of acrylic latex lead to dramatic improvement in film formation at the lower oven drying temperature of 130° C. This leads to improved moisture barrier under these conditions.

At the higher drying temperature of 150° C., the effect on Cobb performance is less marked but still apparent for the acrylic latex blend.

EXAMPLE 9
Stabilisation of PHA latex by acrylic latex

Mixtures of the latices specified in Example 8—in various ratios—were subjected to shear at 1460 sec$^{-1}$ at 20° C. in a Bohlin rheometer with coaxial cylinder geometry. The viscosity of the mixture was measured over a time period until flocculation took place. Table 8 shows the lengths of this period for 4 mixtures.

TABLE 8

| % w/w of second latex | 0 | 1 | 5 | 10 | 15 |
|---|---|---|---|---|---|
| Flocculation time | 200 sec | over 3500 sec | over 3500 sec | over 3500 sec | over 3500 sec |

Using a laboratory stirrer the 5% mixture was found to be stable for over 5 h and the 15% mixture for more than 24 h.

EXAMPLE 10
Latex with steric stabilisation

Example 8 was repeated with the modifications:
(a) a different range of PHA:acrylic ratios was tested; and
(b) each latex contained 3% w/w of "HYPERMER CG6" which is an acrylic graft copolymer emulsifier formulation in water/propylene glycol containing 32% w/w of active agent of HLB number approximately 11–12, available from Imperial Chemical Industries PLC.

Results of the Cobb test are shown in Table 9.

TABLE 9

| Acrylic Polymer | Cobb g m$^{-2}$ | |
|---|---|---|
| % w/w on solids | Oven 130° C., 3 min | IR 150° C., 15s |
| 0 | 61 | 27 |
| 4 | 30 | 5 |
| 8 | 13 | 5 |
| 12 | 14 | 4 |
| 16 | 5 | 4 |
| 20 | 5 | 4 |

With the aid of the emulsifier it is evidently possible to obtain very good Cobb test behaviour at low levels of the non-biodegradable polymer.

We claim:

1. A process for making PHA by producing by fermentation a biomass of micro-organism cells containing PHA and harvesting PHA by decomposing non-PHA cell material (NPCM) by steps including treatment with a surfactant and an oxidant, wherein the oxidant is added before the surfactant; characterised in that the said treatment is applied to the biomass before substantial decomposition of the NPCM by other means.

2. A process for producing a PHA latex of substantial amorphous content by:

(a) forming a biomass containing micro-organism cells containing PHA particles, (b) decomposing the non-PHA cell material of the cells to soluble products;

(c) separating the soluble products from the PHA particles; and (d) forming an aqueous dispersion of PHA particles substantially free of such soluble product:

characterized by carrying out step (c) by resolving the product of step (b) into a solution of the soluble products and a non shear-thickening slurry.

3. A process according to claim 2 in which step (c) is carried out by continuous centrifugation or micro-filtration.

4. A process according to claim 1, wherein the quantity of the surfactant is in the range of 1% to 7% w/w on PHA dry solids.

5. A process according to claim 1, in which the surfactant is selected from the group consisting of $C_{12-16}$ alkyl/about 30 ethoxylate; nonylphenol/about 30 ethoxylate; block copolymer of ethylene oxide and propylene oxide; cetyltrimethylammonium bromide; sodium or ammonium deoxycholate, dodecyl sulphate, N-lauroylsarcosinate dioctyl-sulphosuccinate; and acrylic copolymer emulsifiers.

6. The process according to claim 1, wherein the harvesting step further comprises oxidatively solubilising at least partly the NPCM and applying to the resulting PHA particles a stabilising quantity of surfactant before the PHA has crystallised to the desired extent.

* * * * *

UNITED STATES PATENT AND TRADEMARK OFFICE
CERTIFICATE OF CORRECTION

PATENT NO. : 5,977,250
DATED : November 2, 1999
INVENTOR(S) : Neil George, et. al.

It is certified that error appears in the above-identified patent and that said Letters Patent is hereby corrected as shown below:

Column 22, lines 14 and 15, after subparagraph (a), delete and insert --
(b) decomposing the non-PHA cell material of the cells to soluble products;--

Column 22, line 36, after the word "N-lauroylsarcosinate", insert a comma.

Signed and Sealed this

Second Day of May, 2000

Attest:

Attesting Officer

Q. TODD DICKINSON

Director of Patents and Trademarks